US011952087B2

(12) United States Patent
Myslinski et al.

(10) Patent No.: US 11,952,087 B2
(45) Date of Patent: Apr. 9, 2024

(54) SMART APPAREL AND BACKPACK SYSTEM (71) Applicants: Alessandra E. Myslinski, Sunnyvale, CA (US); William T. Myslinski, Sunnyvale, CA (US); Lucas J. Myslinski, Sunnyvale, CA (US)

(72) Inventors: Alessandra E. Myslinski, Sunnyvale, CA (US); William T. Myslinski, Sunnyvale, CA (US); Lucas J. Myslinski, Sunnyvale, CA (US)

( * ) Notice: Subject to any disclaimer, the term of this patent is extended or adjusted under 35 U.S.C. 154(b) by 707 days.

(21) Appl. No.: 17/118,825

(22) Filed: Dec. 11, 2020

(65) Prior Publication Data

US 2022/0183626 A1 Jun. 16, 2022

(51) Int. Cl.
*B63C 11/04* (2006.01)
*A61B 5/00* (2006.01)
(Continued)

(52) U.S. Cl.
CPC ............ *B63C 11/04* (2013.01); *A61B 5/0004* (2013.01); *A61B 5/0015* (2013.01);
(Continued)

(58) Field of Classification Search
CPC ..... A61B 5/0205; A61B 5/6804; A61B 5/684; A61B 8/4245; A41D 1/00; A41D 1/002; A41D 2400/38; A41D 31/18
See application file for complete search history.

(56) References Cited

U.S. PATENT DOCUMENTS 6,210,771 B1 4/2001 Post et al.
6,341,504 B1 1/2002 Istook
(Continued)

FOREIGN PATENT DOCUMENTS

CA 2821050 1/2014
WO 2005001678 1/2005
WO 2014001843 1/2014

OTHER PUBLICATIONS

Office Action from U.S. Appl. No. 17/118,850.
(Continued)

*Primary Examiner* — Benyam Haile
(74) *Attorney, Agent, or Firm* — Haverstock & Owens, A Law Corporation (57) ABSTRACT A smart clothing and backpack system enables a user to perform many actions. The smart clothing includes circuitry and/or is made of a conductive material enclosed in an insulation material. The smart clothing includes a set of sensors configured to detect body information. The smart clothing includes multiple electromagnets configured to adjust a size of the smart clothing. The electromagnets are configured to have an increased attraction to make the smart clothing tighter on the body of the user. The system includes a smart backpack to communicate with the smart clothing. The smart backpack includes a Radio Frequency IDentification (RFID) reader configured to detect RFID tags on or in items within the smart backpack. Many other features are able to be implemented with the smart clothing and backpack system. The smart clothing is able to include a wetsuit configured to communicate with a surfboard and/or a backpack.

19 Claims, 7 Drawing Sheets (51) Int. Cl.
  *A61B 5/0205* (2006.01)
  *A61B 5/024* (2006.01)
  *A61B 5/11* (2006.01)
  *A61B 5/145* (2006.01)
  *A61B 8/00* (2006.01)
  *B63B 32/50* (2020.01)
  *B63C 11/26* (2006.01)
  *B63C 11/28* (2006.01)
  *A41D 1/00* (2018.01)

(52) U.S. Cl.
  CPC ............ *A61B 5/0205* (2013.01); *A61B 5/024* (2013.01); *A61B 5/1126* (2013.01); *A61B 5/14517* (2013.01); *A61B 5/6804* (2013.01); *A61B 5/6805* (2013.01); *A61B 5/6831* (2013.01); *A61B 5/742* (2013.01); *A61B 5/746* (2013.01); *A61B 8/4245* (2013.01); *B63B 32/50* (2020.02); *B63C 11/26* (2013.01); *B63C 11/28* (2013.01); *A41D 1/002* (2013.01); *A61B 2560/0204* (2013.01); *A61B 2562/08* (2013.01); *B63C 2011/046* (2013.01)

(56) References Cited

U.S. PATENT DOCUMENTS

| | | | |
|---|---|---|---|
| 6,360,615 B1 | 3/2002 | Smela | |
| 6,381,482 B1 | 4/2002 | Jayaraman et al. | |
| 6,543,299 B2 | 4/2003 | Taylor | |
| 6,640,202 B1 * | 10/2003 | Dietz .................. | A41H 1/02 |
| | | | 342/146 |
| 6,687,523 B1 | 2/2004 | Jayaramen et al. | |
| 6,809,462 B2 | 10/2004 | Pelrine et al. | |
| 6,826,968 B2 | 12/2004 | Manaresi et al. | |
| 6,856,715 B1 | 2/2005 | Ebbesen et al. | |
| 6,942,496 B2 | 9/2005 | Sweetland et al. | |
| 6,957,164 B2 | 10/2005 | Dietz et al. | |
| 7,144,830 B2 | 12/2006 | Hill et al. | |
| 7,191,803 B2 | 3/2007 | Orr et al. | |
| 7,230,610 B2 | 6/2007 | Jung et al. | |
| 7,365,031 B2 | 4/2008 | Swallow et al. | |
| 7,413,802 B2 | 8/2008 | Karayianni et al. | |
| 7,468,332 B2 | 12/2008 | Avloni | |
| 7,507,132 B2 | 3/2009 | Grune | |
| 7,559,768 B2 | 7/2009 | Marmarpoulos et al. | |
| 7,592,276 B2 | 9/2009 | Hill et al. | |
| 7,665,288 B2 | 2/2010 | Karayianni et al. | |
| 7,770,473 B2 | 8/2010 | Von Lilienfeld-Toal et al. | |
| 7,781,051 B2 | 8/2010 | Burr et al. | |
| 7,849,888 B2 | 12/2010 | Karayianni et al. | |
| 8,146,171 B2 | 4/2012 | Chung et al. | |
| 8,161,826 B1 | 4/2012 | Taylor | |
| 8,162,857 B2 | 4/2012 | Lanfermann et al. | |
| 8,263,215 B2 | 9/2012 | Burr et al. | |
| 8,290,636 B2 | 10/2012 | Manning | |
| 8,298,968 B2 | 10/2012 | Swallow et al. | |
| 8,308,489 B2 | 11/2012 | Lee et al. | |
| 8,331,097 B2 | 12/2012 | Yang et al. | |
| 8,334,226 B2 | 12/2012 | Nhan et al. | |
| 8,348,865 B2 | 1/2013 | Jeong et al. | |
| 8,362,882 B2 * | 1/2013 | Heubel ................ | D03D 1/0088 |
| | | | 340/407.1 |
| 8,373,079 B2 | 2/2013 | Walkington | |
| 8,393,229 B2 | 3/2013 | Tao et al. | |
| 8,393,282 B2 | 3/2013 | Fujita et al. | |
| 8,536,075 B2 | 9/2013 | Leonard | |
| 8,613,637 B2 | 12/2013 | Puls | |
| 8,627,592 B2 | 1/2014 | Sloop | |
| 8,661,915 B2 | 3/2014 | Taylor | |

| | | |
|---|---|---|
| 8,669,195 B2 | 3/2014 | Swallow et al. |
| 8,704,758 B1 | 4/2014 | Figley et al. |
| 8,730,177 B2 | 5/2014 | Westerman et al. |
| 8,730,192 B2 | 5/2014 | Westerman et al. |
| 8,784,342 B2 | 7/2014 | Hyde et al. |
| 8,800,386 B2 | 8/2014 | Taylor |
| 8,823,639 B2 | 9/2014 | Jackson et al. |
| 8,824,721 B2 | 9/2014 | Zapalac |
| 8,904,876 B2 | 12/2014 | Taylor et al. |
| 8,905,772 B2 | 12/2014 | Rogers et al. |
| 8,929,085 B2 | 1/2015 | Franklin |
| 8,945,328 B2 | 2/2015 | Longinotti-Buitoni et al. |
| 8,948,839 B1 | 2/2015 | Longinotti-Buitoni et al. |
| 9,001,082 B1 | 4/2015 | Rosenberg et al. |
| 9,009,955 B2 | 4/2015 | Slade et al. |
| 9,043,004 B2 | 5/2015 | Casillas et al. |
| 9,055,737 B2 | 6/2015 | Matzel |
| 9,572,378 B2 | 2/2017 | Canales |
| 9,963,210 B1 | 5/2018 | Ebot |
| 10,525,325 B1 | 1/2020 | Koppel |
| 10,736,213 B2 | 8/2020 | Longinotti-Buitoni |
| 11,039,677 B2 | 6/2021 | Clark |
| 2003/0211797 A1 | 11/2003 | Hill et al. |
| 2004/0009729 A1 | 1/2004 | Hill et al. |
| 2005/0069695 A1 | 3/2005 | Jung et al. |
| 2006/0147678 A1 | 7/2006 | Marmaropoulos et al. |
| 2006/0157334 A1 | 7/2006 | Marmaropoulos et al. |
| 2006/0238490 A1 | 10/2006 | Stanley et al. |
| 2006/0281382 A1 | 12/2006 | Karayianni et al. |
| 2007/0049147 A1 | 3/2007 | Hill et al. |
| 2007/0178716 A1 | 8/2007 | Glaser et al. |
| 2007/0202765 A1 | 8/2007 | Krans et al. |
| 2007/0248799 A1 | 10/2007 | DeAngelis et al. |
| 2008/0050550 A1 | 2/2008 | Orth |
| 2008/0105527 A1 | 5/2008 | Leftly |
| 2009/0025819 A1 | 1/2009 | Douglas |
| 2009/0159149 A1 | 6/2009 | Karayianni et al. |
| 2009/0253325 A1 | 10/2009 | Brookstein et al. |
| 2009/0321238 A1 | 12/2009 | Nhan et al. |
| 2010/0219943 A1 | 9/2010 | Ilmari et al. |
| 2011/0018556 A1 | 1/2011 | Le et al. |
| 2012/0030935 A1 | 2/2012 | Slade et al. |
| 2012/0118427 A1 | 5/2012 | Brookstein et al. |
| 2012/0234105 A1 | 9/2012 | Taylor |
| 2012/0313854 A1 | 12/2012 | Senanayake et al. |
| 2012/0323501 A1 | 12/2012 | Sarrafzadeh et al. |
| 2013/0176737 A1 | 7/2013 | Zhou et al. |
| 2013/0229338 A1 | 9/2013 | Sohn et al. |
| 2013/0328783 A1 | 12/2013 | Martin et al. |
| 2014/0070957 A1 | 3/2014 | Longionotti-Buitoni et al. |
| 2014/0088764 A1 | 3/2014 | Naidu et al. |
| 2014/0170919 A1 | 6/2014 | Manipatruni et al. |
| 2014/0318699 A1 | 10/2014 | Longinotti-Buitoni et al. |
| 2015/0040282 A1 | 2/2015 | Longinotti-Buitoni et al. |
| 2015/0091820 A1 | 4/2015 | Rosenberg et al. |
| 2015/0091857 A1 | 4/2015 | Rosenberg et al. |
| 2015/0091859 A1 | 4/2015 | Rosenberg et al. |
| 2015/0113853 A1 | 4/2015 | McKeough |
| 2015/0116920 A1 | 4/2015 | Franklin et al. |
| 2015/0370320 A1 | 12/2015 | Connor |
| 2016/0350639 A1 | 12/2016 | Tere |
| 2019/0265581 A1 | 8/2019 | Calhoun |
| 2022/0407367 A1 | 12/2022 | Mahmood |

OTHER PUBLICATIONS

Montalbano, Elizabeth. This Flexible, Piezoelectric Fabric Turns Kinetic Energy Into Electricity. <https://www.designnews.com/materials-assembly/flexible-piezoelectric-fabric-turns-kinetic-energy-electricity> Published Apr. 5, 2018.

* cited by examiner

SMART APPAREL AND BACKPACK SYSTEM

FIELD OF THE INVENTION

The present invention relates to the field of smart clothing. More specifically, the present invention relates to the field of clothing with computing capabilities.

BACKGROUND OF THE INVENTION

Many smart clothing products are being developed, from sneakers capable of tracking steps to jackets capable of controlling temperature.

SUMMARY OF THE INVENTION

A smart clothing and backpack system enables a user to perform many actions. The smart clothing includes circuitry and/or is made of a conductive material enclosed in an insulation material. The smart clothing includes a set of sensors configured to detect body information. The smart clothing includes multiple electromagnets configured to adjust a size of the smart clothing. The electromagnets are configured to have an increased attraction to make the smart clothing tighter on the body of the user. The system includes a smart backpack to communicate with the smart clothing. The smart backpack includes a Radio Frequency IDentification (RFID) reader configured to detect RFID tags on or in items within the smart backpack. Many other features are able to be implemented with the smart clothing and backpack system.

DETAILED DESCRIPTION OF THE PREFERRED EMBODIMENT

Smart articles of clothing and other objects are described herein. By "smart," the clothing and objects are more capable of performing an additional action beyond merely clothing a user. An example of smart clothing/objects includes clothing/objects that are conductive and/or include circuitry to process information and take an action.

Figure 1:
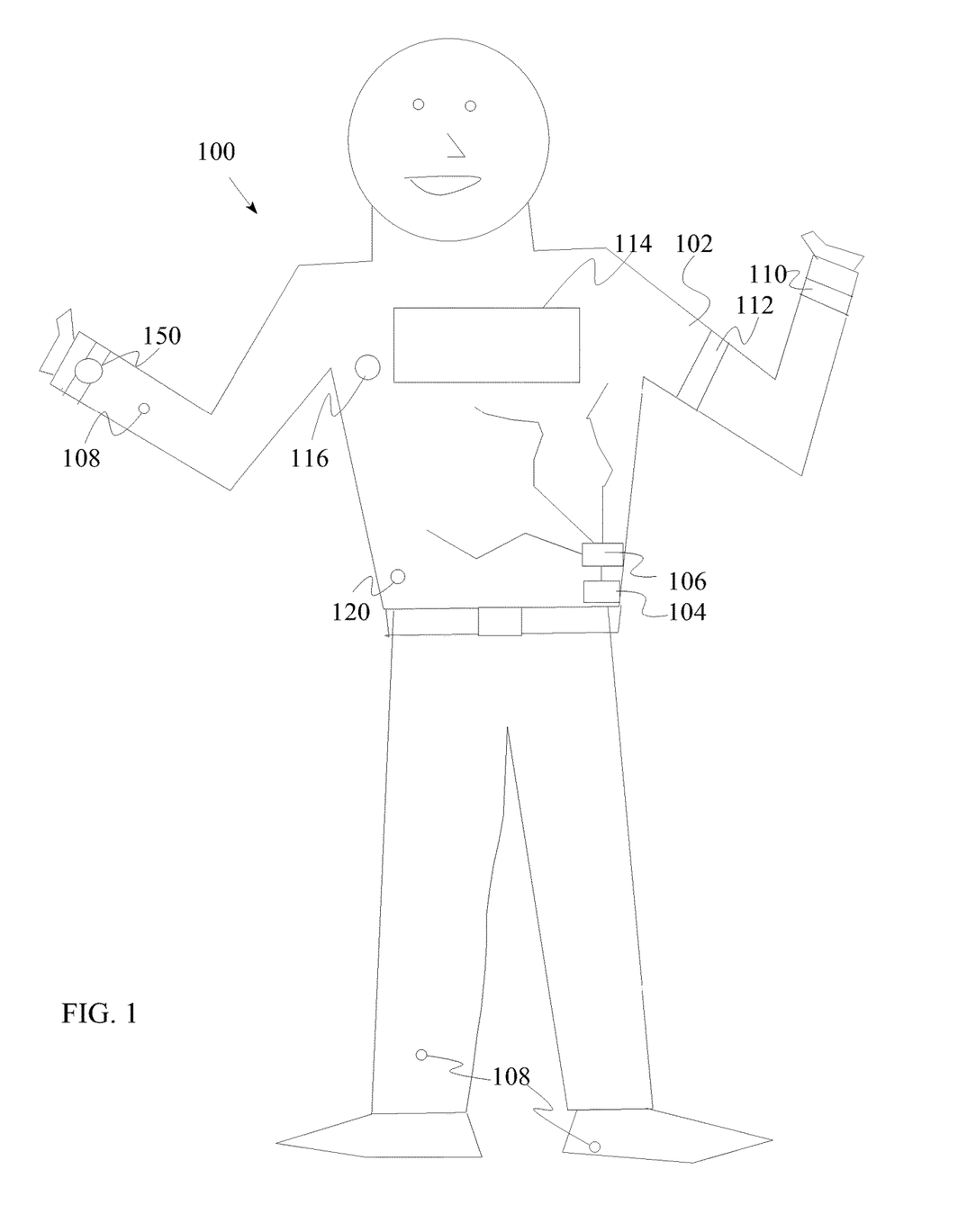
FIG. 1 illustrates a diagram of smart clothing according to some embodiments.

FIG. 1 illustrates a diagram of smart clothing according to some embodiments. The smart clothing 100 is able to include: a material 102 (e.g., fabric, conductive fibers), a power source 104 (e.g., batteries, energy acquisition component), circuitry/computing components 106, one or more sensors 108, an alert/alarm 110, a heating/cooling component 112, a display 114, a camera 116, a transceiver 120 and/or any other components. For clarity, the circuitry/computing components 106 are not shown throughout the smart clothing 100; however, it is understood that the circuitry is able to be as extensive and as distributed throughout the smart clothing 100 as needed. As described herein, the smart clothing 100 is able to include any of the other aspects described herein such as solar strips, perfume compartments, a display, and/or components for adjusting the size/fit of the smart clothing 100. The smart clothing 100 is able to communicate with a mobile device 150 (e.g., smart watch/phone) or any other device.

The smart clothing 100 (or smart objects) are able to include conductive materials such as fibers containing or made of metal such as copper, silver, gold, a non-metal such as graphite or graphene or a combination thereof. In some embodiments, the material 102 of the smart clothing 100 is non-conductive or is an insulator. In some embodiments, the smart clothing 100 includes a mix of materials (e.g., standard clothing material such as cotton, wool, polyester and a strip of a conductive material or spaced, connected threads of a conductive material).

The smart clothing 100 (or objects) are able to include a power source 104 such as a battery, a kinetic energy acquisition component, a friction energy acquisition component, a solar power acquisition component and/or any other power/energy source or acquisition component. In another example, smart clothing or a smart backpack includes a pocket/pouch for receiving one or more rechargeable batteries. Similarly, the smart clothing/objects are able to include circuitry to implement the desired functionality. In some embodiments, the circuitry includes flexible wires (e.g., embedded in the fabric of the smart clothing). In some embodiments, the smart clothing/object is composed of a conductive material which acts as the circuitry. The circuitry is also able to include any other electrical components such as one or more processors/memory to process acquired information (e.g., from the sensors). In some embodiments, the smart clothing 100 includes a power source capable of charging a power source in the smart backpack, or the smart backpack includes a power source capable of charging a power source in the smart clothing 100.

In some embodiments, the smart clothing 100 (or objects) include sensors 108 and/or nano-sensors such as accelerometers to detect specific movements such as exercises, karate moves, and/or parkour moves. Smart clothing is able to be used to determine a user's stride which can later be used in person identification (instead of or in combo with facial recognition). For example, sensors 108 are embedded in the sleeves of each arm of a shirt, in shorts, and sneakers. The sensors 108 are able to be positioned in the clothing in any orientation (e.g., a straight line, in a distributed pattern (e.g., checkerboard), randomly). The sensors 108 are able to function independently or together (even sensors on different articles of clothing). For example, the sensors 108 on the shirt, shorts and sneakers are able to be synchronized to provide real-time movement data (or other data). By using the sensors together, whole body movements are able to be better detected.

In some embodiments, the sensors 108 are able to be grouped or classified to allow more control by a user. For example, if a user wants to focus on arm movements and does not want information from her pants/shorts providing possible extraneous information, the user is able to select the shirt grouping of sensors. The groups are able to be as large or as small as desired (e.g., based on number of sensors or location). For example, a group is limited to one arm, both arms, above or below the belt, one or both legs, and/or one or both feet. Individual or multiple groups are able to be selected. In an example, a group is able to be designated for power-save mode, where only one sensor per square inch (or other area) is activated, while the other sensors are in sleep mode or off mode. In some embodiments, the smart clothing/object automatically puts the sensors in sleep mode when the remaining power level of the batteries or other power source drops below a threshold (e.g., 10%).

Varying types of sensors are able to be used together or the sensors are able to provide varying amounts of data. For example, the sensors are able to determine movement, and the same or other sensors are able to detect an amount a perspiration, temperature, pressure, tension, body information (e.g., heart rate, blood pressure), and/or any other relevant information.

In some embodiments, sensors 108 are included in the smart clothing 100 to track movement and display on a screen the user's movement so the user can see if he is doing movement properly (e.g., yoga, exercises, weight lifting).

In some embodiments, the smart clothing 100 (or object) is able to be included with a healthcare system. For example, the smart clothing 100 is able to include sensors 108 which detect heart rate, blood pressure, sweat amounts, body temperature, external/ambient temperature, sunlight exposure, and/or other health-related data. The smart clothing/object is also able to include devices to respond to the health-related data such as a cooling system for when a user is overheated, a warming system when a user is hypothermic, and/or other devices. The smart clothing/object is able to communicate with other devices such as a phone/watch/server to send and/or receive health-related data.

In some embodiments, the smart clothing 100 is able to detect growth/size changes in a user's body. For example, the smart clothing 100 includes sensors 108 which are configured to measure how far apart they are from each other which would indicate the size of the person's arm, thigh, waist, chest, and so on. Furthering the example, the sensors 108 measure a signal strength or time for a signal to be received, where a lower signal strength or a longer time amount indicates a greater distance between the sensors. In another example, the smart clothing 100 includes a way of measuring the amount of stretching of the material to determine the size of the user's body parts. In some embodiments, the user's footwear includes weight measuring components (e.g., piezoelectric weight sensors) configured to measure the user's weight. For example, each sneaker includes one ore more piezoelectric weight sensors, and the weight detected in each shoe is combined/added together to determine the user's total weight. In some embodiments, the daily growth/size changes are detected/measured and tracked. For example, a user is able to display their daily size changes, so that they can see if there is a trend in their weight (e.g., after exercising and eating better for 7 days straight, a decreasing body size trend is detected). The display is able to be on the user's device (e.g., phone, watch, TV, computer, clothing). In some embodiments, the system is configured to take measurements at the same time or times each day and/or make the comparisons at the same time each day. For example, a user is typically heavier at night than in the morning, so the system is configured to compare the user's size at 7a each day (or another time or times).

In some embodiments, a flexible display 114 is included on the smart clothing 100 (e.g., the shirt's front or back). The display is able to display an image, text and/or video. For example, the display is part of or is coupled to the circuitry and receives signals from a processor as to what to display. Padding is able to be included to protect the user from the display for comfort.

In some embodiments, the smart clothing 100 includes one or more wearable cameras 116. The cameras 116 are able to be embedded in the smart clothing 100 or attached to the smart clothing. The cameras 116 are able to be removable. The content acquired by the cameras 116 is able to be displayed on the flexible display 114 or transmitted to another device (e.g., smart phone, server).

In some embodiments, the smart clothing/object is configured to store kinetic energy. The kinetic energy is stored in a battery/power source 104. The battery 104 is able to be embedded within and/or stored on the smart clothing. The battery 104 is able to be separate from the clothing/object (e.g., a phone device battery). The smart clothing 100 is able to include a flexible, piezoelectric fabric/material which is able to generate storable energy (e.g., stored in the battery 104) based on the movement of the user. For example, as the user swings his arms or walks, the fabric and/or battery 104 in the user's shirt and/or pants is able to store the energy.

As described in: <https://www.designnews.com/materials-assembly/flexible-piezoelectric-fabric-turns-kinetic-energy-electricity> piezoelectric fibers with a piezoelectric shell around an electrically conducting core are able to be used. The piezoelectric fibers are used in combination with other conducting fibers to form an electric circuit connected in series. The fibers are able to generate/harvest energy based on the piezoelectric effect which generates electricity from the deformation of the piezoelectric fibers such as when they are stretched. The material is able to be generated by weaving the piezoelectric fibers with electrically-conducting fibers. The fibers are able to be any size (e.g., as thin as a strand of hair).

In some embodiments, the smart clothing 100 includes a plurality of magnets for generating electricity based on the movement. For example, the magnets are positioned such that when the user moves, the magnets move in relation to electric/conducting fibers, which generates an electric field which is able to be harvested.

Figure 4:
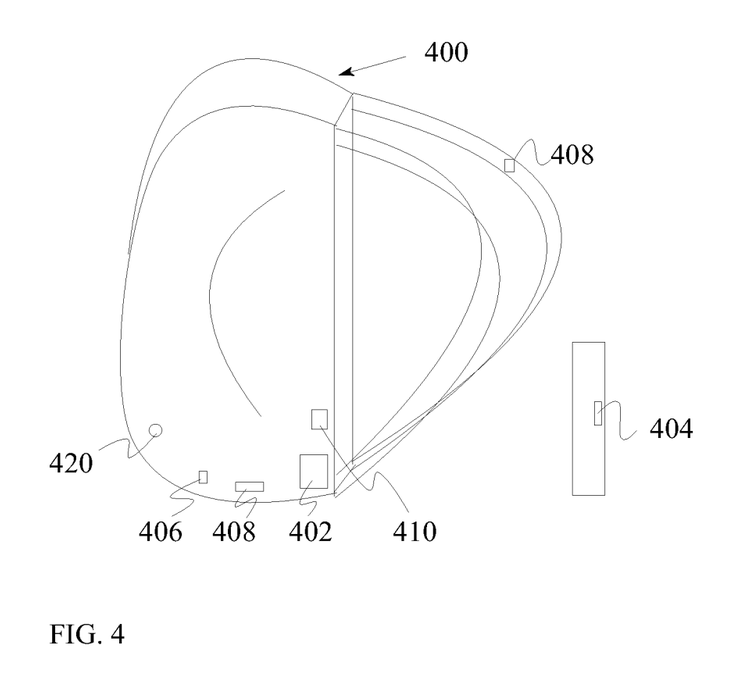
FIG. 4 illustrates a diagram of a smart backpack according to some embodiments.

The smart clothing 100 is able to include a transceiver 120 to communicate with the backpack 400. The transceiver 120 is able to be any implementation such as an antenna, a receiver, a transmitter and/or any combination thereof. Additionally, the transceiver 120 is able to be incorporated in another device such as a small computing device. The transceiver 120 is able to send/receive any wireless communication, digital or analog, such as radio frequency, infrared or Bluetooth®.

The smart clothing 100 described herein is able to include shoes/sneakers/other footwear, socks, pants, underwear, shirts/sweatshirts, skirts/dresses, jackets, hats, face masks and/or any other clothing/apparel. The face masks are able to include sensors to indicate wind/breath flow. The smart clothing 100 is able to communicate with smart jewelry.

Figure 2:
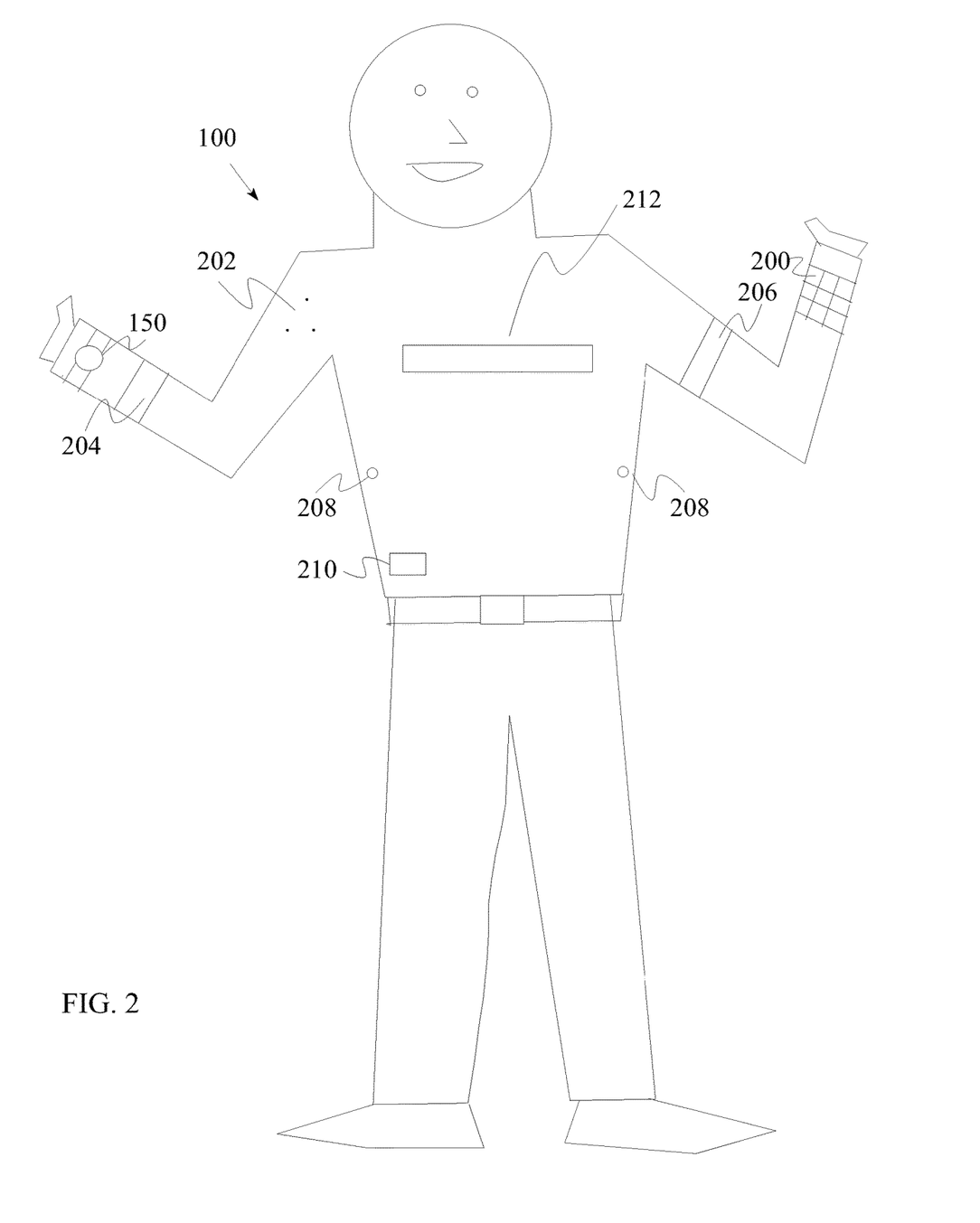
FIG. 2 illustrates a diagram of smart clothing according to some embodiments.

FIG. 2 illustrates a diagram of smart clothing according to some embodiments. The smart clothing 100 (or objects) are able to receive any type of input using an input receiver 200 such as touch-based input and/or gesture-based input. The input is able to be received using an array or a mesh of sensors (e.g., electromagnetic) which are included in (e.g., attached to, part of or embedded in) the material of the smart clothing/objects. The input is able to be received from an external device such as a remote control, a smart phone, and/or another mobile device. The input is able to be received using other means such as audio (e.g., via a microphone), eye movements, and/or brainwaves using an appropriate input receiver.

In some embodiments, the smart clothing 100 (or objects) are waterproof. The waterproofing is able to be implemented in any manner such as a wax layer, a specified material (e.g., Gore-Tex), and/or utilizing waterproof nano-particles. In some embodiments, nano-particles 202 are incorporated with the smart clothing/objects to detect water. The nano-particles 202 are able to communicate with a device (e.g., smart phone) to indicate water detection which is able to trigger an action (e.g., an alert/alarm). The nano-particles 202 are able to be utilized for other functions. The nano-particles 202 are able to be elsewhere (e.g., in/on another object, in/on the user's body) and communicate with the smart clothing 100.

In some embodiments, an alarm clock 204 is able to be included within the smart clothing/objects. The alarm clock 204 is able to be synchronized with a mobile device 150 (e.g., mobile phone or smart watch). The alarm clock 204 is able to include a cooling or warming element embedded or on the smart clothing/object which is able be used to wake up the user. For example, when an alarm is triggered, the smart clothing/object gradually increases (or decreases) in temperature using the heating/cooling element to slowly wake up the user. In some embodiments, the smart clothing/object includes a sound system triggered by the alarm.

In some embodiments, the smart clothing/object includes one or more filters 206 and/or an allergen detector. In some embodiments, the one or more filters 206 are replaceable. The allergen detector is configured to receive airborne allergens or other types of allergens, and then perform a chemical and/or digital analysis of the allergens.

In some embodiments, the smart clothing is able to illuminate. The smart clothing is able to include lights 208 (e.g., LEDs) and/or other devices powered by the smart clothing (e.g., the battery within the smart clothing) or another power source.

In some embodiments, the smart clothing is configured for storing a perfume, cologne or other substance capable of being released/emitted. For example, the smart clothing includes a small capsule 210, which is capable of being triggered to open to release some or all of the stored substance. The capsule 210 is able to be refilled.

In some embodiments, the smart clothing 100 (or object) includes solar panel strips/pieces 212 configured for providing energy as the power source or to the power source.

In some embodiments, the smart clothing 100 is a wetsuit/rash guard, and the smart object is a surfboard/kayak. A wetsuit/rash guard/surfboard/kayak is able to include smart materials/components. The wetsuit is able to include additional heating elements. The surfboard is able to detect sharks or other animals/structures within the water. In some embodiments, the wetsuit/rash guard includes pressure sensors configured to detect water pressure. In some embodiments, the wetsuit/rash guard/surfboard/kayak includes shark protection/detection.

Figure 3:
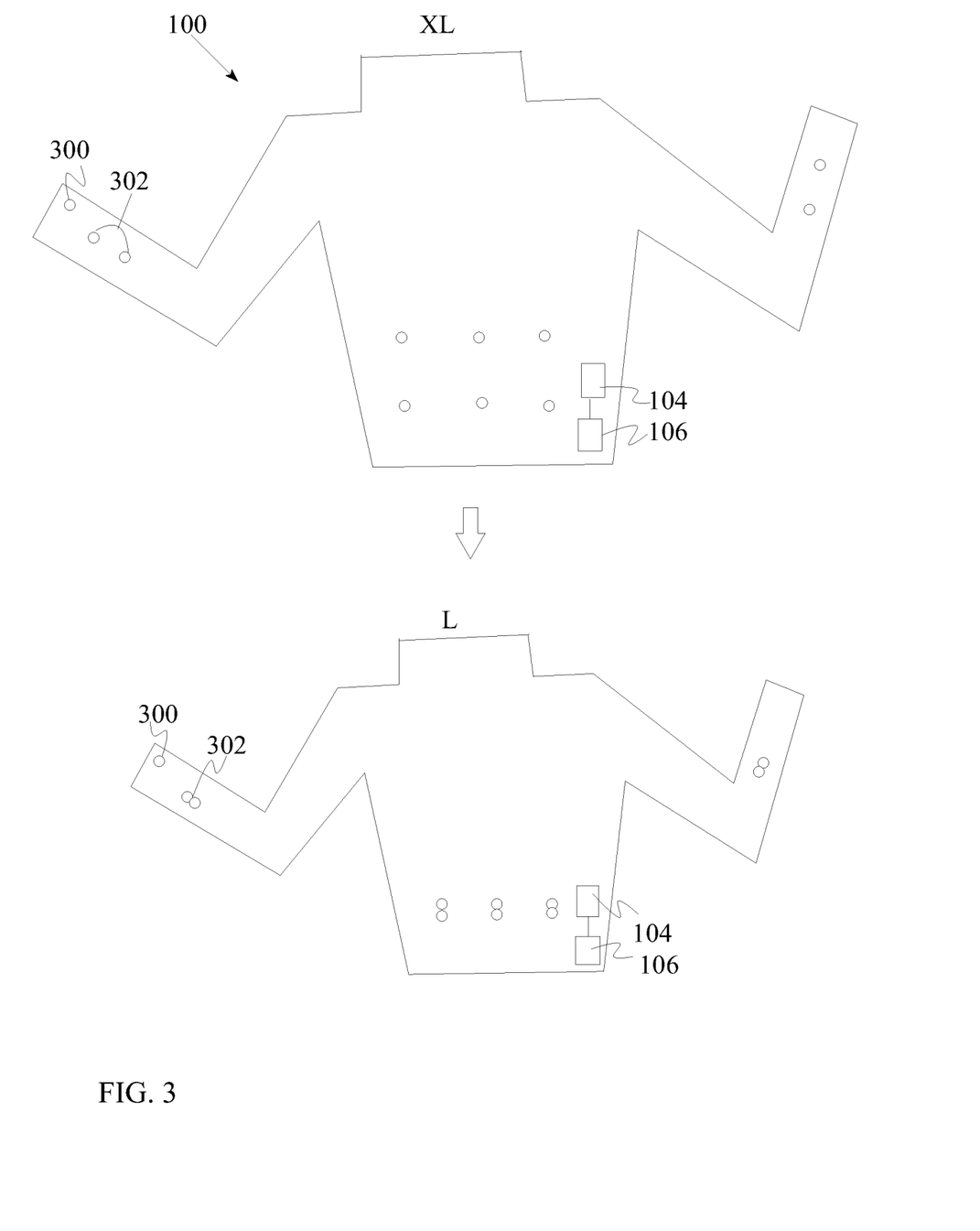
FIG. 3 illustrates a diagram of adjustable smart clothing according to some embodiments.

FIG. 3 illustrates a diagram of adjustable smart clothing according to some embodiments. In some embodiments, the smart clothing 100 is able to adjust how tight/loose the clothing is. A user is able to push a button 300 or the clothing is able to automatically adjust. In some embodiments, electromagnets 302 are utilized to tighten or loosen the smart clothing on the user, and by increasing or decreasing the magnetic strength, the smart clothing will tighten or loosen.

As shown in the Figure, a shirt is a first size (e.g., XL), and then with the push of a button 300 (or another trigger including an automatic trigger), the shirt shrinks to a second size (e.g., L). Upon the push of the button 300, the amount of electricity going to the electromagnets 302 from the power source and the circuitry increases. Similarly, by pressing the button 300 again, the electromagnets are able to be turned off, and the shirt or other article of smart clothing is able to return to the first size.

The electromagnets 302 are positioned on or within the smart clothing 100 so that upon the electromagnets 302 being powered, they will be attracted to each other, and tighten the fabric/clothing. Similarly, when the electromagnets 302 are turned off, they will no longer be attracted to each other, and the fabric/clothing is able to loosen.

In some embodiments, the electromagnets 302 are charged/powered using the kinetic energy acquired by the smart clothing 100 as described herein. For example, as the user swings his arms, electricity is generated and collected using the smart clothing 100 which is then stored in a power source 104 (e.g., battery) and then used to power the electromagnets 302 which adjust the size of the smart clothing 100.

In some embodiments, the smart clothing 100 is able to convert from one type of clothing to another (e.g., long sleeve shirt to short sleeve or pants to shorts). For example, the electromagnets 302 are able to positioned such that when the electromagnets 302 join together they transform the smart clothing 100. For example, positioning several electromagnets 302 at several points in the sleeves of a long sleeve shirt, allows the long sleeve shirt to convert to a short sleeve shirt by pulling the sleeves up as the electromagnets 302 are attracted to each other.

In some embodiments, the smart clothing 100 includes internal threading configured to be pulled to adjust the size of the clothing. For example, an internal thread goes to the sleeve from the collar of a shirt, where a miniature winch (or many winches) are stored within the collar of the shirt which is able to be activated and powered using a power source stored within the smart clothing or an external power source. The thread (via the winch) is able to be released to loosen the shirt.

In some embodiments, the smart clothing includes fibers configured to tighten (e.g., get closer together to shrink the clothing) or loosen to enlarge the clothing. The fibers are able to be magnetic/electromagnetic or attracted in another way. As described herein, when the electromagnets are triggered, they attract to each other to reduce the amount of space between them and tighten the clothing. In some embodiments, the fibers are able to adjust based on moisture (e.g., the fibers tighten when wet, and the fibers loosen when dry).

In some embodiments, the smart clothing includes sensors configured the measure strain/stress of the smart clothing fabric based on movement. Additionally sensors are able to measure other bodily attributes such as breathing (or restrictions) and/or sweating. The acquired sensor information is able to be stored in the circuitry (e.g., processor/memory) and analyzed (or analyzed on another device). Based on the sensed/detected information and analysis, the smart clothing (e.g., polymer fabric and/or electromagnets and/or other implementation) is able to expand or contract in response to movement or other factors such as body temperature. In some embodiments, the expansion or contraction occurs over a delayed period of time (e.g., instead of instantaneously reaction, the contraction is a gradual contraction over 30 seconds or another period of time).

FIG. 4 illustrates a diagram of a smart backpack according to some embodiments. The smart backpack 400 is able to include a Radio Frequency IDentification (RFID) chip reader 402 to confirm that all of a student's books are in the backpack 400. For example, an RFID chip reader 402 is configured to detect RFID chips/tags 404 which are in/on the books.

The smart backpack 400 is able to detect movement via a sensor 406 (e.g., an accelerometer) and then perform the book check, and provide an alert/alarm via the backpack and/or another device (e.g., smart clothing and/or mobile device). The movement sensor 406 is able to be any sensor (e.g., accelerometer, GPS, proximity sensor). For example, the backpack 400 is stationary while the user is in class, so a book check is not necessary, but when the class ends, the user picks up the backpack which is detected by the movement sensor 406 (e.g., determines a movement amount above a threshold). Upon detecting movement, the movement sensor 406 triggers the RFID chip reader 402 or other book detection implementation to check if all of the appropriate books are within the backpack 400. If all of the books are there, then no alert is triggered. If a book is detected as missing, then the backpack 400 is illuminated in a different color (e.g., changes from green to red) or a notification is sent to the user's smart phone, smart watch or exercise band to alert the user that a book is missing. In some embodiments, the specific book (e.g., title) is identified in the alert, or the alert signal provides some other indication of which book is missing (e.g., based on a color code—green equals science book). In some embodiments, another object detection implementation is used instead of RFID such as depth mapping or image/object mapping within the backpack. Although a backpack is described herein, any storage device is able to utilize the implementation described herein such as luggage or a briefcase.

In some embodiments, the backpack 400 includes a sensor 408 for detecting weight (e.g., a piezoelectric sensor is included in one or both of the shoulder straps to detect a weight of the backpack 400, or a weight detection sensor 408 is included on the bottom of the backpack 400. The weight detection sensor 408 is able to be used instead of or in addition to RFID to determine if a book is missing. For example, if each book or object has a specific weight, the weight detection sensor 408 is able to be used to indicate which book is missing.

The smart backpack 400 is not limited to detecting missing books, any item that is able to be detected as missing such as notebooks, pens/pencils, electronics (e.g., tablet/laptop), clothing, and so on. The items are able to be detected using any of the methods described herein.

In an exemplary implementation, the RFID chip reader 402 detects RFID tags 404 for an initialization to generate a database of the items that are stored within the smart backpack 400. For example, the user scans a science book, two math books, a reading book, a language arts book, and a tablet, which all have an RFID chip (or similar component). The smart backpack 400 stores a list (or other data structure) of this information in a memory (along with other processing components/circuitry) 410 contained within the smart backpack. The list is then able to be compared to determine if the books are within the backpack 400 by using the RFID chip reader 402 within the backpack 400. Although an RFID chip reader and an RFID chip are shown, any device capable of detecting objects is able to be implemented. In some embodiments, microchips are placed in/on a book. The RFID chips/tags or microchips are able to be sticky and/or removable. The backpack 400 is able to include a transceiver 420 to communicate with the smart clothing 100. The transceiver 420 is able to be any implementation such as an antenna, a receiver, a transmitter and/or any combination thereof. Additionally, the transceiver 420 is able to be incorporated in another device such as a small computing device. The transceiver 420 is able to send/receive any wireless communication, digital or analog, such as radio frequency, infrared or Bluetooth®.

In another exemplary implementation, the books (or other objects) are inserted into the backpack individually to determine the weight of each one, which is then used to detect if a book or other object is missing when the backpack is moving.

In some embodiments, security measures are implemented to prevent the backpack from being stolen. For example, when the movement sensor detects movement, the backpack attempts to communicate with a mobile device (e.g., wearable device) of the user using near-field communication, Bluetooth® or another communication, and if the communication attempt is unsuccessful, then an alarm is triggered. The alarm is able to be on the backpack and/or at the mobile device. In some embodiments, the backpack includes a trackable implementation which enables the mobile device to locate the backpack (e.g., using GPS).

A backpack or other storage device is able to include an alert system. For example, the backpack changes color as an alert when a book is missing from the backpack. In some embodiments, the backpack (or smart clothing) changes color based on mood. In some embodiments, the backpack includes one or more temperature sensors to trigger the backpack to change color based on the temperature/heat. In some embodiments, the backpack includes extra padding in specific locations to protect an object (e.g., pencil) and also protect the backpack from the object. In some embodiments, the straps of the backpack are configured to tighten. The tightening is able to be implemented automatically (e.g., the backpack detects slack or a loose strap and is configured to tighten until the slack is reduced to a certain point or minimized). In another example, the tightening is able to be implemented based on the user triggering the tightening (e.g., by pushing a button on the backpack or tapping a user's mobile device).

In some embodiments, the smart backpack includes sensors configured the measure strain/stress of the smart backpack material (e.g., in the straps) based on movement. Additionally sensors are able to measure other bodily attributes such as breathing (or restrictions) and/or sweating. Sensors are able to determine the location of the backpack in relation to the user's smart clothing and/or the user's body, and if the smart backpack is in the wrong position relative to the user, the smart backpack straps are able to automatically adjust to properly position the backpack. For example, the back of a user's smart clothing includes a sensor (or device/component) which is configured to communicate with a sensor (or device/component) on the smart backpack which is near the user's back, and if the sensors or other devices are not aligned, then the straps automatically adjust to provide proper alignment or provide a warning/alert for the user to manually adjust the straps for proper alignment. For example, a backpack should rest on a user's hips to take the weight off of his/her back, so the lower portion of the user's shirt or the upper portion of the user's pants is able to include a sensor/device configured to coordinate with a sensor/device in/on the lower portion of the backpack. For example, the smart clothing includes a magnet which triggers the backpack sensor when correctly positioned, but does not trigger the sensor when the backpack is incorrectly positioned (e.g., too high on the user's back). The acquired sensor information is able to be stored in the circuitry (e.g., processor/memory) and analyzed (or analyzed on another device). Based on the sensed/detected information and analysis, the smart backpack straps or other component (e.g., polymer fabric and/or electromagnets and/or other implementation) are able to expand or contract in response to movement or other factors such as body temperature. In some embodiments, the expansion or contraction occurs over a delayed period of time (e.g., instead of instantaneously reaction, the contraction is a gradual contraction over 30 seconds or another period of time).

In some embodiments, the smart clothing includes and/or communicates with a backpack, including a self-tightening backpack. Similar to how to the smart clothing is self-tightening, the backpack is able to include electromagnetic components which when triggered attract to each other and tighten the straps of the backpack. Additionally, the straps are able to be attached to a motorized component capable of pulling the straps tighter by pulling one way, and pulling the straps looser by pulling another way.

In some embodiments, the smart clothing is configured to change color based on mood. Mood is able to be determined based on physiological signs (e.g., heart rate, blood pressure, sweat amount, and/or other detectable signs). For example, a wearable device (e.g., exercise band, smart watch) is able to detect and acquire physiological information. Furthering the example, a smart watch acquires a user's heart rate and sweat amount, and then the smart watch and/or another device (e.g., processing component in the smart clothing) analyzes the heart rate and sweat amount to determine the user's mood. For example, if the user's heart rate is above a threshold, and the sweat amount is above a threshold, then the user's mood is determined to be "excited." Any number of thresholds are able to be implemented, and any number of variables are able to be analyzed. For example, if the user's heart rate is above a second threshold, the user's mood is determined to be "stressed." The wearable device is able to send a trigger to the smart clothing (e.g., a signal where 1="excited," 2="stressed," 3="happy" and so on). The smart clothing is then able to take an action such as changing colors of lights/LEDs on the smart clothing or changing the display on the smart clothing to reflect the user's current mood. A user's mood is able to be determined based on other information as well such as analyzing the user's communications (e.g., text/SMS messages, emails, phone calls, social media posts, web page posts), audio analysis, and/or facial expressions/physical appearance. For example, communications are able to be analyzed to detect keywords such as happy, sad, angry, or specific phrases which connote an emotion such as, "I'm so stressed" or "There's so much pressure." In another example, a user device is able to analyze audio from the user such as detecting laughing, crying, a user's tone, the volume of the user's voice and/or any other audio signals that may indicate the user's mood. In another example, a user device is able to be used to analyze a video and/or scan of the user's face and/or actions to determine the user's mood. For example, templates are able to be used to detect a smile versus a frown versus crying. The various implementations are able to be used together or separately to determine a user's mood.

In some embodiments, footwear (e.g., sneakers, shoes, socks) include circuitry to count a user's steps and/or other exercise information. The footwear is able to communicate with other devices (e.g., mobile device, smart clothing).

In some embodiments, a time keeping device (e.g., watch) is embedded within clothing (e.g., shorts or a shirt) configured with touch capabilities to enable a user to tap the device to start/stop the device or is configured to automatically start/stop based on detected movement.

In some embodiments, the smart clothing is configured to glow in the dark using solar-powered capabilities. For example, the smart clothing includes a solar panel and power storage or other power source which is able to power lights or other items that would allow the smart clothing to glow in the dark.

Figure 5:
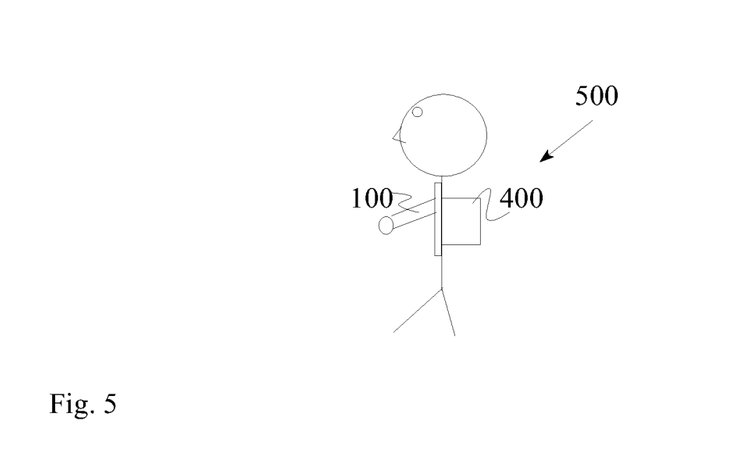
FIG. 5 illustrates a diagram of a system of smart clothing with a smart backpack according to some embodiments.

FIG. 5 illustrates a diagram of a system of smart clothing with a smart backpack according to some embodiments. The smart clothing-backpack system 500 includes the smart clothing 100 as described herein and the smart backpack 400 as described herein.

The smart clothing 100 is able to automatically adjust the tightness/size of the clothing. The smart clothing 100 is able to transition from shorts to pants, pants to shorts, long sleeve to short sleeve, or short sleeve to long sleeve. The smart clothing 100 is able to change patterns. The smart clothing 100 is able to utilize a screen to display content. The smart clothing 100 is able to implement solar cells/panels to provide power to components on the clothing (e.g., a solar-powered glow in the dark shirt). The smart clothing 100 is able to communicate with the smart backpack 400. Content is able to be communicated between the smart clothing 100 and the smart backpack 400. The content is able to be communicated wirelessly or via a wired implementation. Electricity is also able to be communicated between the smart clothing 100 and the smart backpack 400. For example, a power source on/in the smart backpack 400 is able to provide energy to a display, an alarm, lights, and/or another component on the smart clothing 100. In another example, the smart backpack 400 is able to communicate an alert (e.g., a book is missing from the backpack) to the smart clothing 100 for the smart clothing 100 to sound an alarm.

The smart backpack 400 is able to include any of the features described herein such as an implementation to detect a missing object (e.g., book), different lighting features, and/or self-tightening straps.

In some embodiments, the smart clothing 100 and/or the smart backpack 400 are able to communicate with another device (e.g., smart phone, smart jewelry, personal computer).

Figure 6:
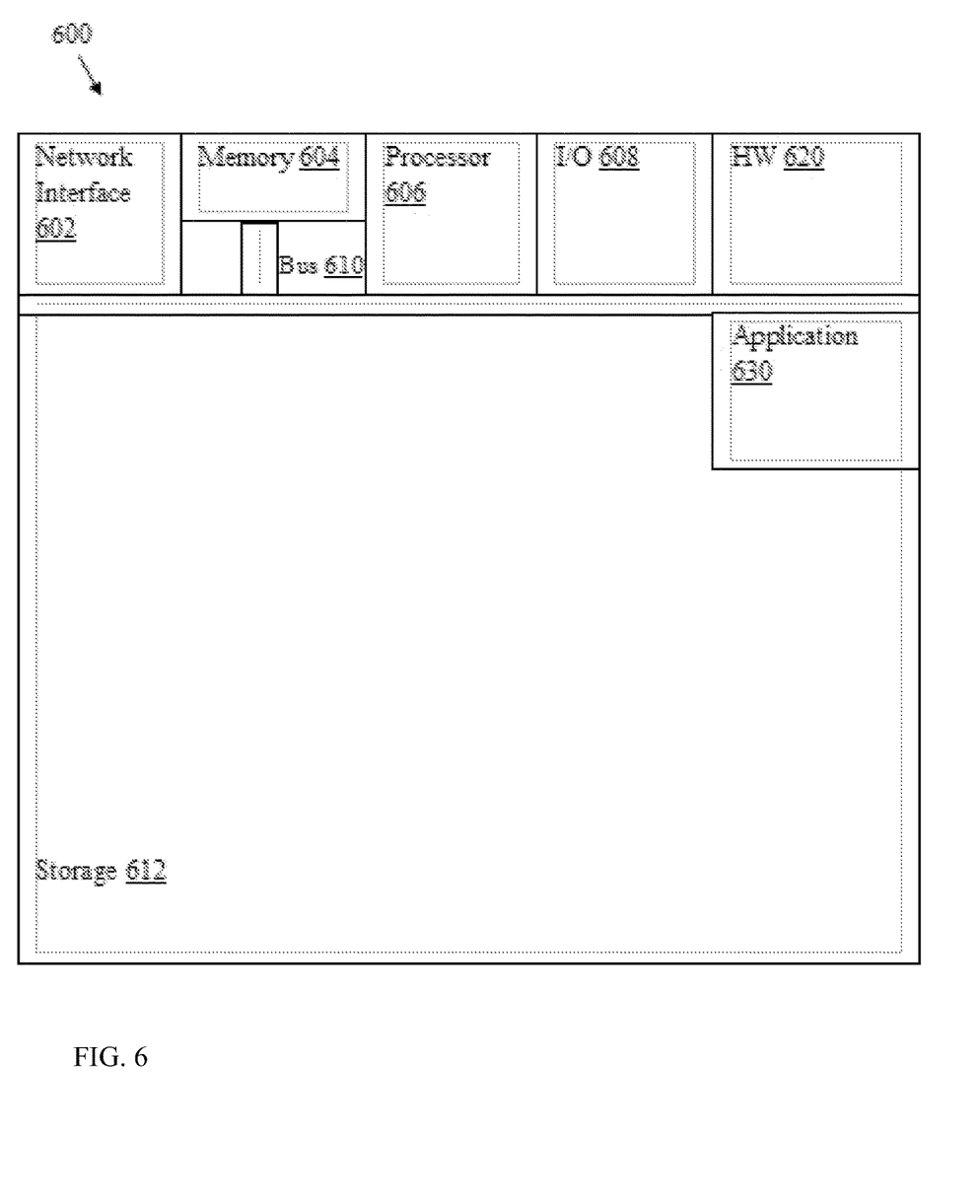
FIG. 6 illustrates a block diagram of an exemplary computing device configured to be utilized with the smart clothing/backpack according to some embodiments.

FIG. 6 illustrates a block diagram of an exemplary computing device 600 configured to be utilized with the smart clothing/backpack according to some embodiments. The computing device 600 is able to be used to acquire, store, compute, process, communicate and/or display information including, but not limited to, text, images, videos and audio. In some examples, the computing device 600 is able to be used to monitor, process, and analyze the information. In general, a hardware structure suitable for implementing the computing device 600 includes a network interface 602, a memory 604, a processor 606, I/O device(s) 608, a bus 610 and a storage device 612. The choice of processor is not critical as long as a suitable processor with sufficient speed is chosen. The memory 604 is able to be any conventional computer memory known in the art. The storage device 612 is able to include a hard drive, CDROM, CDRW, DVD, DVDRW, flash memory card, solid state drive or any other storage device. The computing device 600 is able to include one or more network interfaces 602. An example of a network interface includes a network card connected to an Ethernet or other type of LAN. The I/O device(s) 608 are able to include one or more of the following: keyboard, mouse, monitor, display, printer, modem, touchscreen, touchpad, speaker/microphone, voice input device, eye detection, infrared detection, hologram detection, button interface, hand-waving, body-motion capture, touchless 3D input, joystick, remote control, brain-computer interface/direct neural interface/brain-machine interface, camera, and other devices. In some embodiments, the hardware structure includes multiple processors and other hardware to perform parallel processing. Smart clothing/backpack application(s) 630 used to perform the monitoring, processing, analyzing, taking actions and any other steps are likely to be stored in the storage device 612 and memory 604 and processed as applications are typically processed. More or fewer components shown in FIG. 6 are able to be included in the computing device 600. In some embodiments, smart clothing/backpack hardware 620 is included. Although the computing device 600 in FIG. 6 includes applications 630 and hardware 620 for implementing smart clothing/backpack features, the smart clothing/backpack method is able to be implemented on a computing device in hardware, firmware, software or any combination thereof. For example, in some embodiments, the smart clothing/backpack applications 630 are programmed in a memory and executed using a processor. In another example, in some embodiments, the smart clothing/backpack hardware 620 is programmed hardware logic including gates specifically designed to implement the method.

In some embodiments, the smart clothing/backpack application(s) 630 include several applications and/or modules. Modules include a monitoring module for monitoring information, a processing module for processing (e.g., converting) information, and an analysis module for analyzing information. In some embodiments, modules include one or more sub-modules as well. In some embodiments, fewer or additional modules are able to be included. In some embodiments, the applications and/or the modules are located on different devices. For example, a device performs monitoring, processing, and analyzing, but the taking an action is performed on a different device, or in another example, the monitoring and processing occurs on a first device, the analysis occurs on a second device, and the action is taken on a third device. Any configuration of where the applications/modules are located is able to be implemented such that the smart clothing/backpack is executed.

Examples of suitable computing devices include, but are not limited to a personal computer, a laptop computer, a computer workstation, a server, a mainframe computer, a handheld computer, a personal digital assistant, a pager, a telephone, a fax machine, a cellular/mobile telephone, a smart appliance, a gaming console, a digital camera, a digital camcorder, a camera phone, a smart phone/device (e.g., a Droid® or an iPhone®), a portable music player (e.g., an iPod®), a tablet (e.g., an iPad®), a video player, an e-reader (e.g., Kindle™), a DVD writer/player, an HD (e.g., Blu-ray®) or ultra high density writer/player, a television, a copy machine, a scanner, a car stereo, a stereo, a satellite, a DVR (e.g., TiVo®), a smart watch/jewelry, smart clothing, smart objects (e.g., backpack), nano devices, micro devices, smart devices, a home entertainment system or any other suitable computing device.

Figure 7:
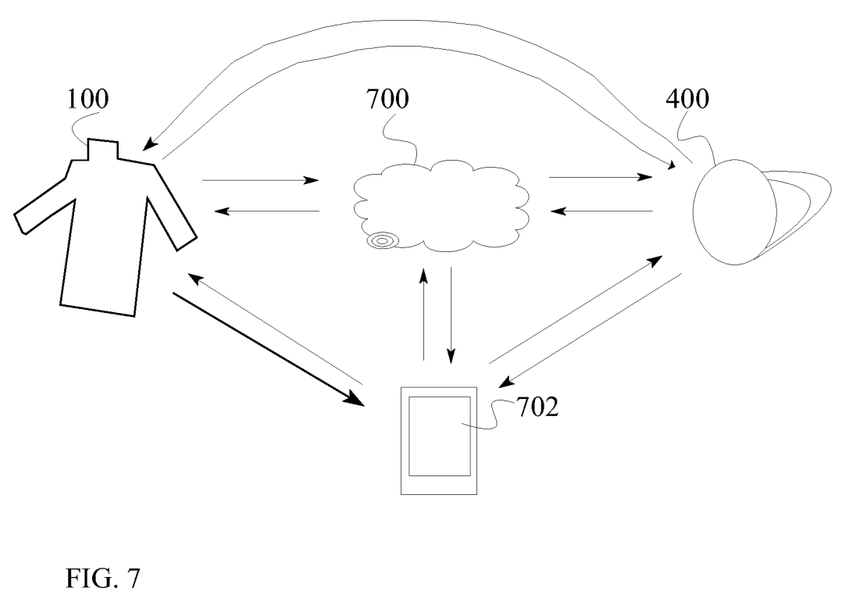
FIG. 7 illustrates a network of devices according to some embodiments.

FIG. 7 illustrates a network of devices according to some embodiments. The network of devices is able to include any number of devices and any various devices including, but not limited to, smart clothing 100, a smart backpack 400 and a computing device (e.g., a PC, smart phone) 702 coupled through a network 700. The smart clothing 100 is able to communicate with a smart backpack 400 and/or a computing device 702 directly or via a network 700. The network 700 is able to be any network or networks including, but not limited to, the Internet, an intranet, a LAN/WAN/MAN, WiFi, wireless, wired, Ethernet, cellular, 4G/5G/xG, satellite, a combination of networks, or any other implementation of communicating. The devices are able to communicate with each other through the network 700 or directly to each other. The network 700 is able to include one or more servers or other devices to implement cloud storage/computing (e.g., one or more of the devices is able to be an end user device, a server, a cloud device, a company and/or another entity).

Figure 8:
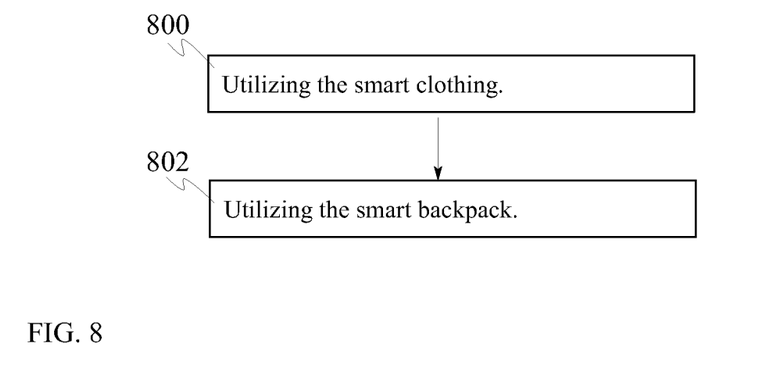
FIG. 8 illustrates a flowchart of a method of utilizing smart clothing and/or a smart backpack according to some embodiments.

FIG. 8 illustrates a flowchart of a method of utilizing smart clothing and/or a smart backpack according to some embodiments. In the step 800, smart clothing is utilized. Utilizing the smart clothing is able to include any standard steps of wearing the clothing, and implementing any of the functions of the smart clothing as described herein such as: adjusting the size of the smart clothing, detecting pressures, implementing protection measures, re-configuring the smart clothing, presenting a display on the smart clothing, performing exercise measurements/analysis, presenting an alarm, implementing a power source (e.g., kinetic, solar-powered), and communicating with another device (e.g., smart backpack, computing device). In the step 802, a smart backpack is utilized. Utilizing the smart backpack includes detecting objects in the backpack (and when objects are missing from the backpack), communicating with the smart clothing (e.g., communicating a signal to the smart clothing, or communicating power to the smart clothing), and/or communicating with a computing device. In some embodiments, the order of the steps is modified. In some embodiments, fewer or additional steps are implemented. In some embodiments, the steps are implemented independently. For example, the smart clothing is utilized without the smart backpack, or vice versa. In some embodiments, another object is utilized (e.g., a surfboard).

Figure 9:
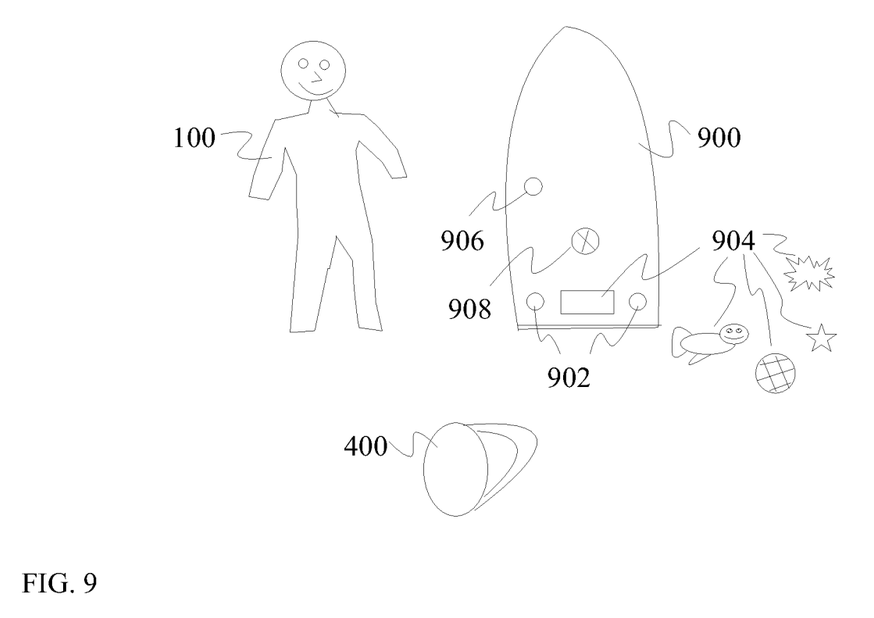
FIG. 9 illustrates a diagram of a system of a smart clothing and smart object according to some embodiments.

FIG. 9 illustrates a diagram of a system of a smart clothing and smart object according to some embodiments. As described herein the smart clothing 100 is a wetsuit or a rash guard, and the smart object 900 is a surfboard or kayak. The wetsuit/rash guard and the surfboard/kayak are able to include smart materials/components. The wetsuit is able to include additional heating elements. For example, embedded within the wetsuit are conductive coils configured to warm the user. The coils are able to be insulated to prevent shocking the user.

The surfboard/kayak is able to include motion sensors, cameras, and/or other sensors 902 configured to detect sharks or other animals/structures within the water. The cameras/sensors are able to be positioned on the board to detect animals/objects coming from any direction, 360 degrees. The motion sensor (including a heat sensor in some embodiments) is able to be implemented in any manner such as a device configured at the bottom/underside of the surfboard/kayak to send a signal to detect movement in the water, or a device configured to detect heat signatures wherein if a size of a heat signature is above a threshold, an object is determined to be a threatening animal (e.g., shark). For example, the surfboard includes software/app configured for analyzing the size of an object including comparing the size of the object with a threshold size. The size of the object is able to be determined using depth information (e.g., a depth map), and based on how far the object is and the detected signal/image, the size of the object is able to be calculated and/or estimated. Furthering the example, images/videos are able to be acquired/generated, and the frames of each image are able to be compared in sequence to determine a delta between each frame along with the depth/distance of the object such that a rate of size change is able to be determined to establish the animal/object size. In some embodiments, sonar and/or other depth finding implementations are utilized to determine the depth/distance of the animal/object. For example, a small fish at 1 foot away from the surfboard may be the size of a great white shark at 200 feet away, so by knowing the distance of the animal/object, a better determination of the animal/object is able to be made. The distance of the object is able to be used in determining whether to trigger an alert. For example, a distance threshold is used where if the animal/object is closer than the distance threshold, then an alert is sent. If a shark is detected but is 200 yards away, then an alert may not be triggered, but if the threshold is 50 feet, and the shark is 49 feet away, then an alert is triggered. The lighting system is able to include different colors such as yellow lights for within a first threshold, orange within a second threshold and red within a third threshold, where each threshold is a shorter distance from the surfboard (e.g., 50 feet, 25 feet and 10 feet). In some embodiments, the speed of the animal/object is factored in (e.g., if the animal is moving faster than a speed threshold, then an alert is triggered). For example, if the animal detect is moving at 20 mph, where the speed threshold is 15 mph, then an alert is triggered, but slower fish will not trigger an alert. Object templates are also able to be used to assist in classifying an animal/object. For example, the shape of a shark is very different from the shape of an octopus. The alerts are also able to be triggered based on proximity to a coral reef. For example, many surfers are injured by hitting coral reefs under the water, so an alert notifying the user that a coral reef is within a specified distance may help warn the user that they are in potential danger.

The surfboard/kayak is able to include countermeasures 904 to protect against an animal attack. The countermeasures 904 are able to include a flashing light, a speaker system to produce audible sounds which distract, repel or confuse the animal, a net, a decoy and/or any other countermeasure. For example, speakers are embedded in the surfboard, and when a motion sensor detects a shark within a specified range (e.g., within 5 feet), the speakers emit a sound that is audible to sharks and distracts, confuses or repels them. In another example, the surfboard includes a lighting system configured to flash upon the motion sensor detecting a shark, where the lighting system confuses/repels the shark. The lighting system is also able to include lights on top of the board to alert the user that a shark is within a specified range, and/or lights on the bottom of the board to distract, confuse or repel the shark. In another example, the surfboard includes a storage compartment configured for storing a net and/or a decoy which are able to be triggered to be ejected (e.g., chemical reaction-based propulsion upon mixing with water, or hydraulically) or dropped from the surfboard. The decoy is able to be any object that may distract an attacking shark such as a rubber-based seal or a more environmentally-friendly decoy such as a wooden seal. In some embodiments, the decoy is self-inflating similar to an airbag to enable a smaller storage footprint, but a large enough decoy to prevent a shark attack on the person. In another example, a shark repellant chemical is able to be emitted upon detection of a shark. In some embodiments, the wetsuit/rash guard includes pressure sensors configured to detect water pressure.

The wetsuit/rash guard and surfboard/kayak combination is able to include a smart backpack 400 as well. The smart backpack is able to be the same as or similar to the smart backpack described herein with some modifications such as being waterproof, water resistant or at least acceptable to get wet. The smart backpack is able to be used to provide any of the features described herein such as detecting objects within the backpack. The user is able to use the backpack to ensure that he does not forget items such as booties, flippers, sunscreen and any other items. The backpack is also able to store a power source and/or processing components (e.g., a power source to provide power to the surfboard/kayak and/or the wetsuit. The backpack is able to communicate with the wetsuit/rash guard and/or the surfboard/kayak. The surfboard/kayak (or other water craft) is able to communicate with the wetsuit/rashguard and/or smart backpack using a transceiver 906 (e.g., using WiFi, RF, infrared, Bluetooth or others). The surfboard/kayak is able to communicate any signal or message such as an alert trigger. The surfboard/kayak is able to include any of the components described herein for other devices.

In some embodiments, the smart surfboard/kayak or other water craft includes a hydroelectric power generator 908. For example, a small propeller under the surfboard is able to be used to generate power based on the motion of the surfboard through the water. Any hydroelectric power generation system is able to be implemented. The bulk of the power generation system is able to be stored within the surfboard or kayak.

In some embodiments, smart clothing, a smart wetsuit, a smart backpack, a smart surfboard, a smart device and/or any combination thereof are able to be used together. For example, a user wears a self-adjusting smart shirt with a smart backpack and a smart surfboard. The shirt, backpack and surfboard are able to communicate and perform any of the other features described herein. In another example, the user wears a smart shirt and smart backpack, and switches to a smart wetsuit with a smart surfboard, where all of the smart items are able to communicate with each other.

An exemplary implementation is described herein. The smart clothing includes conductive materials such as fibers containing or made of metal such as copper, silver, gold, a non-metal such as graphite or graphene or a combination thereof. The conductive materials are able to be enclosed in insulating materials such as wool, cotton and/or other fabrics/materials. The smart clothing includes a power source such as a battery, a kinetic energy acquisition component, a friction energy acquisition component, a solar power acquisition component and/or any other power/energy source or acquisition component. The smart clothing includes circuitry to implement any desired functionality. In some embodiments, the circuitry includes flexible wires (e.g., embedded in the fabric of the smart clothing). In some embodiments, the smart clothing/object is composed of a conductive material which acts as the circuitry. The circuitry is also able to include any other electrical components such as one or more processors to process/analyze acquired information (e.g., from the sensors). For example, a small battery and a microprocessor are embedded in the collar of a shirt or in the sole of a shoe/sneaker.

The smart clothing includes sensors and/or nano-sensors such as accelerometers to detect specific movements such as exercises, karate moves, and parkour moves. For example, sensors are embedded in the sleeves of each arm of a shirt, the chest/stomach/back area of a shirt, in shorts, and sneakers. The sensors are able to be positioned in the clothing in any orientation (e.g., a straight line, in a distributed pattern (e.g., checkerboard), randomly). The sensors on the shirt, shorts, sneakers and/or other clothing are able to be synchronized to provide real-time movement data (or other data). For example, the sensors are able to determine movement, and the same or other sensors are able to detect an amount a perspiration, temperature, pressure, tension, body information (e.g., heart rate, blood pressure), and/or any other relevant information. For example, a sweat sensor is able to be included in a shirt which is configured to detect water. In another example, a smart watch is able to monitor a heart rate. The smart clothing/object is also able to include devices to respond to the health-related data such as a cooling system for when a user is overheated, a warming system when a user is cold/hypothermic, and/or other devices. The smart clothing/object is able to communicate with other devices such as a phone/watch/server/backpack to send and/or receive health-related data.

The smart clothing is able to detect growth/size changes in a user's body. For example, the smart clothing includes sensors which are configured to measure how far apart they are from each other which would indicate the size of the person's arm, thigh, waist, chest, and so on. For example, sensors within the smart clothing (such as in the sleeves) are able to send signals to each other, and based on the amount of time for the signal to be received, it is able to be determined how far apart the sensors are, and then based on the distance, if the distance has increased, it is based on the user's body growing and causing the clothing to pull which in turn pulls the sensors apart. In another example, the smart clothing includes a way of measuring the amount of stretching of the material to determine the size of the user's body parts. For example, a tension sensor is included within the smart clothing, and when the tension is above a threshold, then the shirt is determined to be too tight, so the smart clothing is able to be expanded in size. The user's footwear includes weight measuring components (e.g., piezoelectric weight sensors) configured to measure the user's weight. For example, each sneaker includes one or more piezoelectric weight sensors, and the weight detected in each shoe is added together to determine the user's total weight. Based on the user's weight or a delta of weight (e.g., tracking the user's weight over a period of time), the smart clothing is able to increase or decrease in size.

The smart clothing/object is configured to store kinetic energy. The kinetic energy is stored in a battery/power source. The battery is able to be embedded within and/or stored on the smart clothing. The battery is able to be separate from the clothing/object (e.g., a phone device battery or stored in a smart backpack). The smart clothing is able to include a flexible, piezoelectric fabric/material which is able to generate, storable energy (e.g., stored in the battery) based on the movement of the user. For example, as the user swings his arms or walks, the fabric and/or battery in the user's shirt and/or pants is able to store the energy. The piezoelectric fibers are used in combination with other conducting fibers to form an electric circuit connected in series. The fibers are able to generate/harvest energy based on the piezoelectric effect which generates electricity from the deformation of the piezoelectric fibers such as when they are stretched. The material is able to be generated by weaving the piezoelectric fibers with electrically-conducting fibers. The fibers are able to be any size (e.g., as thin as a strand of hair). Similarly, the energy generated by the force/impact of walking/running is able to be stored.

The smart clothing includes a plurality of magnets for generating electricity based on the movement. For example, the magnets are positioned such that when the user moves, the magnets move in relation to electric/conducting fibers which generates storable energy.

The smart clothing is able to adjust how tight/loose the clothing is. A user is able to push a button, or the clothing is able to automatically adjust. In some embodiments, the smart clothing starts in a loose orientation, and automatically shrinks to a tight/fitted orientation. For example, the smart clothing decreases in size until sensors within the smart clothing detect a specified amount of stretch/pull (e.g., above a threshold) to trigger a circuit breaker to stop the shrinkage of the smart clothing. In some embodiments, electromagnets are utilized to tighten or loosen the smart clothing on the user, and by increasing or decreasing the magnetic strength, the smart clothing will tighten or loosen. A shirt is a first size (e.g., XL), and then with the push of a button, the shirt shrinks to a second size (e.g., L). Upon the push of the button, the amount of electricity going to the electromagnets from the power source and the circuitry increases. In some embodiments, the electromagnetism increases to the point where the electromagnets attract to each other enough to actually join together which shrinks the shirt size. By pressing the button again, the electromagnets are able to be turned off, and the shirt or other article of smart clothing is able to return to the first size.

The electromagnets are charged/powered using the kinetic energy acquired by the smart clothing as described herein. For example, as the user swings his arms, electricity is generated and collected using the smart clothing which is then stored in a power source (e.g., battery) and then used to power the electromagnets which adjust the size of the smart clothing.

The smart clothing is able to convert from one type of clothing to another (e.g., long sleeve shirt to short sleeve or pants to shorts). For example, the electromagnets are able to positioned such that when the electromagnets join together they transform the smart clothing. For example, positioning several electromagnets at several points in the sleeves of a long sleeve shirt, allows the long sleeve shirt to convert to a short sleeve shirt by pulling the sleeves up as the electromagnets are attracted to each other.

The smart clothing receives any type of input using an input receiver such as touch-based input and/or gesture-based input. The input is able to be received using an array or a mesh of sensors (e.g., electromagnetic) which are included in (e.g., attached to, part of or embedded in) the material of the smart clothing/objects. The input is able to be received from an external device such as a remote control, a smart phone, and/or another mobile device. The input is able to be received using other means such as audio (e.g., via a microphone), eye movements, and/or brainwaves using an appropriate input receiver.

The smart clothing is able to be waterproof. The smart clothing is able to be configured to change color based on mood.

An alarm/alert (e.g., alarm clock, warning system) is able to be included within the smart clothing/objects. The alarm clock is able to be synchronized with a mobile device (e.g., mobile phone or smart watch). The alarm clock is able to include a cooling or warming element embedded in or on the smart clothing/object which is able be used to wake up the user. For example, when an alarm is triggered, the smart clothing/object gradually increases (or decreases) in temperature using the heating/cooling element to slowly wake up the user (e.g., an increase of 1 degree/second or 1 degree/3 seconds until a limit is reached). In some embodiments, the smart clothing/object includes a sound system triggered by the alarm. The alarm/alert is able to be triggered in another manner as well such as by receiving a signal from another device (e.g., backpack).

The smart clothing is able to illuminate. The smart clothing is able to include lights (e.g., LEDs) and/or other devices powered by the smart clothing (e.g., the battery within the smart clothing) or another power source. The smart clothing is able to include solar panel strips/pieces.

In some embodiments, the smart clothing is a wetsuit/rash guard. A wetsuit/rash guard is able to include smart materials/components. The wetsuit is able to include additional heating elements. In some embodiments, the wetsuit/rash guard includes pressure sensors configured to detect water pressure. In some embodiments, the wetsuit/rash guard includes shark protection/detection.

A flexible display is included on the smart clothing (e.g., the shirt's front or back). The display is able to display an image and/or video. The content on the display is able to be modified based on a user's mood (e.g., based on physiological analysis as described herein). The display is able to be used to display an alert/alarm (e.g., book missing). The display is also able to be used to display medical, healthcare and/or physical information of the user.

The smart clothing is able to include one or more wearable cameras. The cameras are able to be embedded in the smart clothing or attached to the smart clothing. The cameras are able to be removable. The content acquired by the cameras is able to be displayed on the flexible display or transmitted to another device (e.g., smart phone, server).

The smart clothing described herein is able to include shoes/sneakers/other footwear, socks, pants, underwear, shirts/sweatshirts, dresses, jackets, hats, face masks and/or any other clothing/apparel. The face masks are able to include sensors to indicate wind/breath flow.

The smart clothing is configured to communicate with a smart backpack and/or another device. The smart backpack is able to include a self-tightening backpack. Similar to how to the smart clothing is self-tightening, the backpack is able to include electromagnetic components which when triggered attract to each other and tighten the straps of the backpack. Additionally, the straps are able to be attached to a motorized component capable of pulling the straps tighter by pulling one way, and pulling the straps looser by pulling another way.

The smart backpack is able to include a Radio Frequency IDentification (RFID) chip reader to confirm that all of student's books are in the backpack. For example, an RFID chip reader is configured to detect RFID chips/tags which are in/on the books and/or other items.

The smart backpack is able to detect movement via a sensor (e.g., an accelerometer) and then perform the book check, and provide an alert/alarm via the backpack and/or other mobile device. The movement sensor is able to be any sensor (e.g., accelerometer, GPS, proximity sensor). For example, the backpack is stationary while the user is in class, so a book check is not necessary, but when the class ends, the user picks up the backpack which is detected by the movement sensor (e.g., determines a movement amount above a threshold). Upon detecting movement, the movement sensor triggers the RFID chip reader or other book detection implementation to check if all of the appropriate books are within the backpack. If all of the books are there, then no alert is triggered. If a book is detected as missing, then the backpack is illuminated in a different color (e.g., changes from green to red) or a notification is sent to the user's smart phone, smart watch or exercise band to alert the user that a book is missing. In some embodiments, the specific book (e.g., title) is identified in the alert.

In some embodiments, the backpack includes a sensor for detecting weight (e.g., a piezoelectric sensor is included in one or both of the shoulder straps to detect a weight of the backpack, or a weight detection sensor is included on the bottom of the backpack. The weight detection sensor is able to be used instead of or in addition to the movement sensor or RFID reader to determine if a book is missing.

The smart backpack is not limited to detecting missing books, any article/item that is able to be detected as missing such as notebooks, pens/pencils, electronics (e.g., tablet/laptop), clothing, exercise equipment, work materials, personal materials, and so on. The articles/items are able to be detected using any of the methods described herein. In another exemplary implementation, the books (or other objects) are inserted into the backpack individually to determine the weight of each one, which is then used to detect if a book or other object is missing when the backpack is moved/moving.

Security measures are implemented to prevent the backpack from being stolen. For example, when the movement sensor detects movement, the backpack attempts to communicate with a mobile device (e.g., wearable device) of the user using near-field communication, Bluetooth® or another communication, and if the communication attempt is unsuccessful, then an alarm is triggered. The alarm is able to be on the backpack, the smart clothing and/or at the mobile device. In another example, if a mobile device and/or backpack detect that they are a distance apart greater than a threshold, then an alarm is triggered. In some embodiments, the backpack includes a trackable implementation which enables the mobile device to locate the backpack (e.g., using GPS).

A backpack or other storage device is able to include an alert system. For example, the backpack changes color and/or sounds an audible alarm as an alert when a book is missing from the backpack. In some embodiments, the backpack (or smart clothing) changes color based on mood. In some embodiments, the backpack includes one or more temperature sensors to trigger the backpack to change color based on the temperature/heat. In some embodiments, the backpack includes extra padding in specific locations to protect an object (e.g., pencil) and also protect the backpack from the object. In some embodiments, the straps of the backpack are configured to tighten. The tightening is able to be implemented automatically (e.g., the backpack detects slack or a loose strap and is configured to tighten until the slack is reduced to a certain point or minimized). In another example, the tightening is able to be implemented based on the user triggering the tightening (e.g., by pushing a button on the backpack or tapping a user's mobile device).

To utilize the smart clothing/backpack system, a user wears the smart clothing (e.g., any clothing item such as a shirt, pants, jacket, sneakers, socks, hat and so on) and a smart backpack (or other storage device). The smart clothing and the smart backpack each have components to enable "smart" functionality such as power sources, conductive materials, sensors, RFID readers, and so on as described herein. The smart clothing and the smart backpack are able to communicate with each other to perform functions such as the smart backpack sending a signal to the smart clothing to provide an alert.

In operation, the smart clothing and backpack provide many advantages over standard clothing and backpacks. For example, the smart clothing is able to adjust in size, display information, provide warmth or cooling, and many other features. Additionally, the smart backpack is able to detect missing items and communicate information to the smart clothing or another device.

Although some implementations and/or embodiments have been described related to specific implementations and/or embodiments, and some aspects/elements/steps of some implementations and/or embodiments have been described related to specific implementations and/or embodiments, any of the aspects/elements/steps, implementations and/or embodiments are applicable to other aspects/elements/steps, implementations and/or embodiments described herein.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:

1. A system comprising:
   smart clothing comprising:
      circuitry comprising a conductive material enclosed in an insulation material, wherein the circuitry comprises a processor and a memory;
      a plurality of sensors configured to detect body information of a user including:
         a first set of sensors configured to detect an amount of sweat,
         a second set of sensors configured to detect a heart rate, and
         a third set of sensors configured to detect size changes in a body of the user by sending a signal to each other, determining an amount of time for the signal to reach each sensor, and computing a distance based on the amount of time, wherein the plurality of sensors are configured in a checkerboard pattern in the smart clothing;
      a plurality of electromagnets configured to adjust a size of the smart clothing, wherein the plurality of electromagnets are configured to have an increased attraction when triggered on to make the smart clothing tighter on the body of the user;
      a first transceiver;
      a first power source configured to provide power to the plurality of sensors, the plurality of electromagnets, and the first transceiver through the circuitry; and
   a smart backpack configured to communicate with the smart clothing comprising:
      a Radio Frequency IDentification (RFID) reader configured to detect RFID tags on or in items within the smart backpack;
      one or more lights;
      a second transceiver configured to communicate with the first transceiver; and
      a second power source configured to provide power to the RFID reader, the one or more lights and the second transceiver.

2. The system of claim 1 wherein the plurality of sensors further comprise a fourth set of sensors configured to determine a weight of the user.

3. The system of claim 1 wherein the smart backpack further comprises at least one motion sensor configured for detecting motion of the backpack, wherein the second transceiver communicates a signal to the first transceiver for the smart clothing to provide an alert to the user.

4. The system of claim 1 wherein the smart clothing further comprises a flexible piezoelectric material configured to generate storable energy when the user moves.

5. The system of claim 1 wherein the plurality of electromagnets are configured to convert the smart clothing from a first type of clothing to a second type of clothing.

6. The system of claim 1 wherein the smart clothing further comprises an alerting device configured to alert the user.

7. The system of claim 6 wherein the alerting device comprises a heating device configured to gradually become warmer to alert the user, or a cooling device configured to gradually become cooler to alert the user.

8. The system of claim 1 wherein the smart clothing further comprises light emitting diodes configured to be illuminated, wherein the light emitting diodes change color based on a mood of the user, wherein the mood of the user is determined based on physiological information.

9. The system of claim 1 wherein the smart clothing further comprises a display configured to display content, wherein the content displayed changes based on a mood of the user, wherein the mood of the user is determined based on physiological information.

10. The system of claim 1 wherein the RFID tags are removable.

11. The system of claim 1 wherein the one or more lights of the smart backpack are configured to change color based on an alert.

12. The system of claim 1 wherein the smart backpack comprises automatically adjustable straps, wherein the automatically adjustable straps are configured to tighten using electromagnets.

13. The system of claim 1 wherein the smart backpack comprises adjustable straps and a first set of one or more positional sensors, and the smart clothing comprises a second set of one or more positional sensors, wherein when the first set of one or more positional sensors are not aligned with the second set of one or more positional sensors, an alert is triggered on the smart backpack and/or the smart clothing.

14. The system of claim 1 wherein the smart clothing comprises footwear configured to acquire exercise information.

15. The system of claim 1 wherein the smart clothing comprises a time-keeping device including a stopwatch configuration configured to be activated using a touch sensor on or in the smart clothing.

16. The system of claim 1 wherein the first power source and/or the second power source comprise a solar panel for acquiring energy.

17. The system of claim 1 wherein the second power source uses inductive charging to charge the first power source.

18. The system of claim 1 wherein the smart clothing is further configured to glow in the dark.

19. A method comprising:
   wearing smart clothing, the smart clothing comprising:
      circuitry comprising a conductive material enclosed in an insulation material, wherein the circuitry comprises a processor and a memory;
      a plurality of sensors configured to detect body information of a user including:
         a first set of sensors configured to detect an amount of sweat,
         a second set of sensors configured to detect a heart rate, and
         a third set of sensors configured to detect size changes in a body of the user by sending a signal to each other, determining an amount of time for the signal to reach each sensor, and computing a distance based on the amount of time, wherein the plurality of sensors are configured in a checkerboard pattern in the smart clothing;

a plurality of electromagnets configured to adjust a size of the smart clothing, wherein the plurality of electromagnets are configured to have an increased attraction to make the smart clothing tighter on the body of the user;

a first transceiver;

a first power source configured to provide power to the plurality of sensors, the plurality of electromagnets, and the first transceiver through the circuitry; and wearing a smart backpack configured to communicate with the smart clothing, the smart backpack comprising:

a Radio Frequency IDentification (RFID) reader configured to detect RFID tags on or in items within the smart backpack;

one or more lights;

a second transceiver configured to communicate with the first transceiver; and a second power source configured to provide power to the RFID reader, the one or more lights and the second transceiver.

* * * * *